United States Patent [19]
Kurtis

[11] Patent Number: 5,509,408
[45] Date of Patent: Apr. 23, 1996

[54] NEONATAL RESUSCITATION DEVICE

[75] Inventor: Peter S. Kurtis, West Hartford, Conn.

[73] Assignee: Vital Signs, Inc., Totowa, N.J.

[21] Appl. No.: 214,398

[22] Filed: Mar. 16, 1994

Related U.S. Application Data

[63] Continuation-in-part of Ser. No. 842,612, Feb. 27, 1992, abandoned, which is a continuation-in-part of Ser. No. 398,782, Aug. 25, 1989, abandoned, which is a continuation-in-part of Ser. No. 361,730, Jun. 2, 1989, abandoned, which is a continuation of Ser. No. 96,222, Sep. 4, 1987, abandoned, which is a continuation of Ser. No. 25,326, Mar. 13, 1987, abandoned.

[51] Int. Cl.$^6$ .................................................. A61M 16/04
[52] U.S. Cl. ........................... 128/207.14; 128/200.26; 604/27; 604/19; 604/37
[58] Field of Search .................. 128/207.14, 207.16, 128/200.26; 604/19, 23, 27, 28, 30, 35–40, 43, 45, 48–49, 54, 93, 118, 119, 164, 165, 173, 181, 187, 246, 247, 280–286

[56] References Cited

U.S. PATENT DOCUMENTS

| | | | |
|---|---|---|---|
| 2,269,823 | 6/1942 | Kreiselman | 604/280 |
| 3,175,557 | 3/1965 | Hammond | 128/207.14 |
| 3,964,488 | 6/1976 | Ring et al. | 128/207.14 |
| 4,787,894 | 11/1988 | Turnbull | 128/207.14 |

OTHER PUBLICATIONS

Respiratory therapy equipment, McPherson, 1981–pp. 166–167.

*Primary Examiner*—Edgar S. Burr
*Assistant Examiner*—William J. Deane, Jr.
*Attorney, Agent, or Firm*—R. Gale Rhodes, Jr.

[57] ABSTRACT

Combination for suctioning a neonatal infant having a mouth, a trachea and a pathway having a generally curved shape extending from said mouth to said trachea, including a generally elongated endotracheal tube including a wall and having a proximate end and a distal end and including an upper section and a lower section shorter in length the upper section, the lower section being flexible and the upper section including at least a portion which is substantially rigid for a length of at least the length of and a curvature substantially conforming to the curvature of the pathway from the mouth to the trachea of the neonatal infant; a connector including an upper portion for being connected to a source of suctioning and a cylindrical lower portion for being connected to the proximate end of the endotracheal tube; the endotracheal tube having a lumen extending therethrough and the connector having a conduit extending therethrough, the lumen and the conduit combining to form a suctioning passageway; and an adapter provided on one of the upper sections of the endotracheal tube and the lower cylindrical portion of the connector and the adapter provided with an adapter passageway in fluid communication with the suctioning passageway, the adapter provided at a location which remains outside of the mouth of the infant while the infant is being suctioned and the adapter passageway being provided with an entrance opening for venting the suctioning passageway.

39 Claims, 5 Drawing Sheets

NEONATAL RESUSCITATION DEVICE

CROSS-REFERENCE TO RELATED APPLICATIONS

This application is a continuation-in-part of Ser. No. 842,612, filed Feb. 27, 1992, now abandoned, which is a continuation-in-part of application Ser. No. 398,782, filed Aug. 25, 1989, now abandoned, which is a continuation-in-part of application Ser. No. 361,730, filed Jun. 2, 1989, now abandoned, which is a continuation of application Ser. No. 096,222, filed Sep. 4, 1987, now abandoned, which is a continuation of application Ser. No. 025,326, filed Mar. 13, 1987, now abandoned. The content of each of those applications is hereby incorporated by reference.

BACKGROUND OF THE INVENTION

Approximately 10–15% of all infants pass meconium or fetal stools while still in the womb. Meconium is thick viscous particulate fluid. This condition is often due to the fetus experiencing a degree of hypoxia or lack of oxygen before birth. A serious problem faced in the delivery room during the birthing process involves the resuscitation of infants who have passed meconium in utero so that the meconium is aspirated into the pharynx and the trachea of the infant. Meconium aspiration can cause severe respiratory distress, and if the meconium is not thoroughly removed from the infant's air passageway, that is, the pharynx and trachea, before the infant begins to breath, there is a danger of developing illnesses such as pneumonia, sepsis, pneumothorax and persistent pulmonary hypertension which could result in the severe damage or death of the infant.

The presently accepted method of resuscitation of neonatal or newborn infants with meconium in their pharynx and trachea is set forth in the MANUAL OF NEONATAL CARE by Cloherty and Stark, Second Edition, Little Brown and Company, pages 203 to 206 (1985). The method involves a tedious procedure of suctioning the meconium out of the infant's pharynx and trachea by mouth, through an endotracheal tube (ETT).

In this procedure, a physician in one hand operates a laryngoscope, an instrument having a handle attached to a metal blade, which is inserted in the patient's mouth to open the patient's mouth. Any fluid is then suctioned from the mouth using a catheter which is in the physician's other hand. When the fluid is cleared from the mouth, the physician removes the catheter, puts it down and picks up an endotracheal tube. At this point, the metal blade portion of the laryngoscope is positioned in the patient's mouth to deflect the tongue and epiglottis in order to visualize the vocal cords. The endotracheal tube is inserted past the epiglottis, through the vocal cords and into the trachea. The laryngoscope is then removed from the patient's mouth to free the physician's hand to remove the stylet which is inside the passageway of the endotracheal tube. The stylet maintains the rigidity of the endotracheal tube while it is being inserted into the air passageway. While the stylet is necessary to maintain the rigidity of the endotracheal tube to assist in directing the tube past the vocal cords, the stylet must be removed from the tube after intubation in order to clear the tube to suction meconium. At this point, the physician suctions the trachea of the infant by mouth, through the endotracheal tube, to remove the meconium while withdrawing the tube. The proximal end of the endotracheal tube, which is in the physician's mouth, may be covered by a piece of gauze or by the physician's surgical mask while suctioning, to avoid contact with the meconium. However, the gauze or mask does not totally protect the physician from getting meconium into his mouth. Once the tube is withdrawn from the infant's mouth, the endotracheal tube must be cleared of meconium by blowing through the tube, and the stylet again reinserted so the procedure may be repeated. Alternatively, two or three additional endotracheal tubes and stylets must be immediately available. The laryngoscope must then be reinserted into the infant's pharynx and the entire intubation and suctioning procedure must be repeated in order to remove the meconium thoroughly. Typically, this procedure is repeated two to four times.

Once the meconium is cleared from the infant's trachea, the patient requires ventilation to provide oxygen to, and remove carbon dioxide from, the lungs. While this can often be done with an ambu bag and mask, it is far more effective to reintube the infant. Using currently accepted methods, the endotracheal tube must be cleared of meconium by blowing through the tube and the stylet reinserted, or, alternatively, an additional endotracheal tube and stylet is utilized. The laryngoscope is again repositioned in the mouth to visualize the vocal cords. The patient is then intubated and the laryngoscope is removed so the physician can remove the stylet with his free hand. The patient then may be ventilated using an ambu bag, which is attached to the endotracheal tube, to pump air through the larynx and trachea into the lungs. If the patient's heart rate is still slow, the ambu bag is removed from the endotracheal tube and medication is administered directly through the endotracheal tube. The ambu bag is then reattached to the endotracheal tube to force the medication into the infant's lungs and provide further ventilation.

The above-described procedure to remove meconium has several drawbacks. It is very inefficient in that it takes many steps to perform thoroughly and takes a relatively long period of time. Meconium must be removed from the pharynx and trachea of an infant before the infant takes its first breath. The longer it takes for the infant to start breathing, the higher the risk of brain, heart, kidney or other organ damage. Another problem resulting from the use of this method is the risk to the physician suctioning the meconium by mouth through the endotracheal tube. While it is common to put a gauze or surgical mask over the end of the endotracheal tube and suck through the gauze pad or surgical mask, there is still a danger of having the meconium come in contact with the physician's mouth. If this happens, serious infectious agents such as gonorrhea, hepatitis, or AIDS may be transmitted to the physician. This risk is especially acute in dealing with infants born to intravenous drug users, since a substantial number of them, perhaps as many as 75%, carry the HIV (AIDS) virus, which is present in body fluid such as meconium. This is a particular problem for pediatricians and other health care professionals involved in neonatal resuscitation who are routinely called into the delivery room shortly before or just after an infant is born and has developed a problem. In the emergency, it may be impossible to brief the pediatrician or other health care professional on the entire medical history of the infant's mother.

SUMMARY OF THE INVENTION

It is therefore an object of the invention to provide a device and method for neonatal resuscitation which can rapidly and efficiently remove meconium from the pharynx and trachea of an infant and which will avoid mouth contact of the meconium by the physician during suctioning.

It is an additional object of the invention to provide a device and method which allows the physician to rapidly and easily perform multiple intubations of a neonatal infant using a single endotracheal tube in a manner which does not require the insertion and removal of a stylet in the endotracheal tube during its use thereby minimizing the length of time necessary to treat the patient with suction, oxygen or medication.

It is another object of the invention to provide an endotracheal tube which has an upper section which is substantially rigid in a predetermined shape and self supporting in clinical operation and has a lower section which is flexible and will not puncture or cause damage to a patient's airway when the endotracheal tube is in use.

It is an object of the invention to provide an endotracheal tube which a physician can hold at a location where the device can be most easily manipulated and, using a single hand, not only provide suction to a patient but also selectively eliminate or limit suction at the distal end of the endotracheal tube in order to minimize trauma to the vocal cords and trachea while the endotracheal tube is used, to permit easier insertion of the endotracheal tube into the trachea, and to allow more efficient removal of meconium.

It is also an object of the invention to provide a device and method which permits the use of a single endotracheal tube to provide suctioning of the patient's airway, the direct administration of oxygen into, and the removal of carbon dioxide from, a patient's lungs after suctioning and also the administration of medication without interrupting the supply of oxygen to the patient.

It is another object of the invention to provide a device and method which allows the user to easily control the administration of oxygen and removal of carbon dioxide with an ambu bag to the neonatal infant.

It is a further object of the invention to provide a device and method for clearing meconium from a neonatal infant which allows the physician to continually visualize the vocal cords during suctioning of the mouth and trachea.

In one illustrative embodiment the tube has a rigid upper section which is supported by a shape support member which substantially conforms to the shape of the pathway from the mouth to the trachea of the neonatal infant patient and which is of a length which is at least as long as that pathway. The tube has a flexible lower section and a port located in the tube at a point where the endotracheal tube will be held by the physician during suctioning. The location of the port which communicates directly with the lumen in the endotracheal tube allows the physician to provide suctioning to the patient while the port is covered or partially covered and allows the physician to vent the endotracheal tube so there is no or minimal suction at the distal end of the tube when the port is open.

In further embodiments, the port is provided with an adapter which can be used to connect a device, such as a syringe, to dispense medication through the endotracheal tube to the patient. Additionally, the proximate end of the tube may be provided with a connector which is attached to a mechanized source of suction if suction is needed or, optionally, to a source of oxygen if the patient needs oxygen.

In a further illustrative embodiment, the invention includes a combination for suctioning a neonatal infant having a mouth, a trachea and a pathway having a generally curved shape extending from said mouth to said trachea, including a generally elongated endotracheal tube including a wall and having a proximate end and a distal end and including an upper section and a lower section shorter in length than the upper section, the lower section being flexible and the upper section including at least a portion which is substantially rigid for a length of at least the length of and a curvature substantially conforming to the curvature of the pathway from the mouth to the trachea of the neonatal infant; a connector including an upper portion for being connected to a source of suctioning and a cylindrical lower portion for being connected to the proximate end of the endotracheal tube; the endotracheal tube having a lumen extending therethrough and the connector having a conduit extending therethrough, the lumen and the conduit combining to form a suctioning passageway; and an adapter provided on one of the upper sections of the endotracheal tube and the lower cylindrical portion of the connector and the adapter provided with an adapter passageway in fluid communication with the suctioning passageway, the adapter provided at a location which remains outside of the mouth of the infant while the infant is being suctioned and the adapter passageway being provided with an entrance opening for venting the suctioning passageway.

These and other features and advantages of the invention will be more readily understood from the following description of certain preferred embodiments, when read with the accompanying drawings.

DESCRIPTION OF THE PREFERRED EMBODIMENTS

Figure 1:
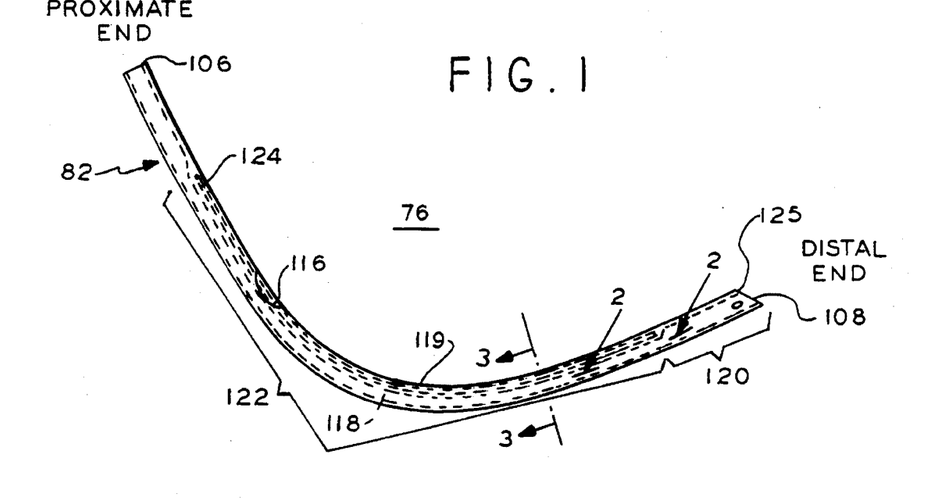
FIG. 1 is a side view of the resuscitation device.
Figure 2:
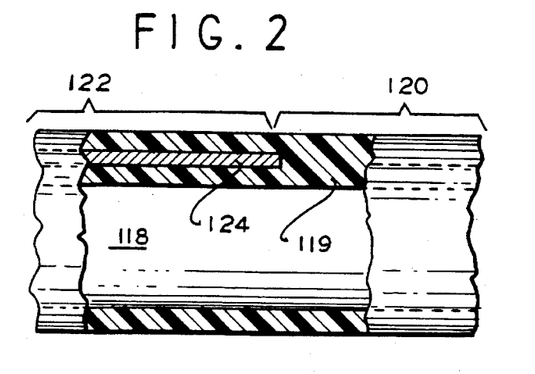
FIG. 2 is a side view, partly in cross-section, of a part of the endotracheal tube along the lines 2—2 in FIG. 1.
Figure 3:
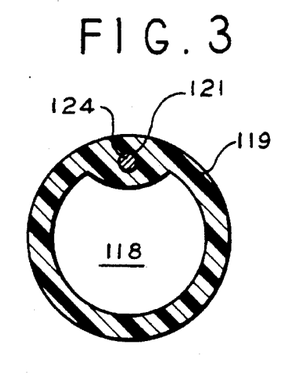
FIG. 3 is a cross-sectional view of the endotracheal tube along the lines 3—3 in FIG. 1.

Referring to FIGS. 1, 2 and 3 the resuscitation device 76 includes an endotracheal tube 82 having a rigid upper section 122, a flexible lower section 120 and a venting port 116 in the outer wall 119 of the endotracheal tube 82. The endotracheal tube 82 is also provided with an entry port 106 in the proximate end and an exit port 108 in the distal end. The entry port 106 and exit port 108 are connected by main lumen 118 which passes through the elongated cylindrical endotracheal tube 82.

Figure 4:
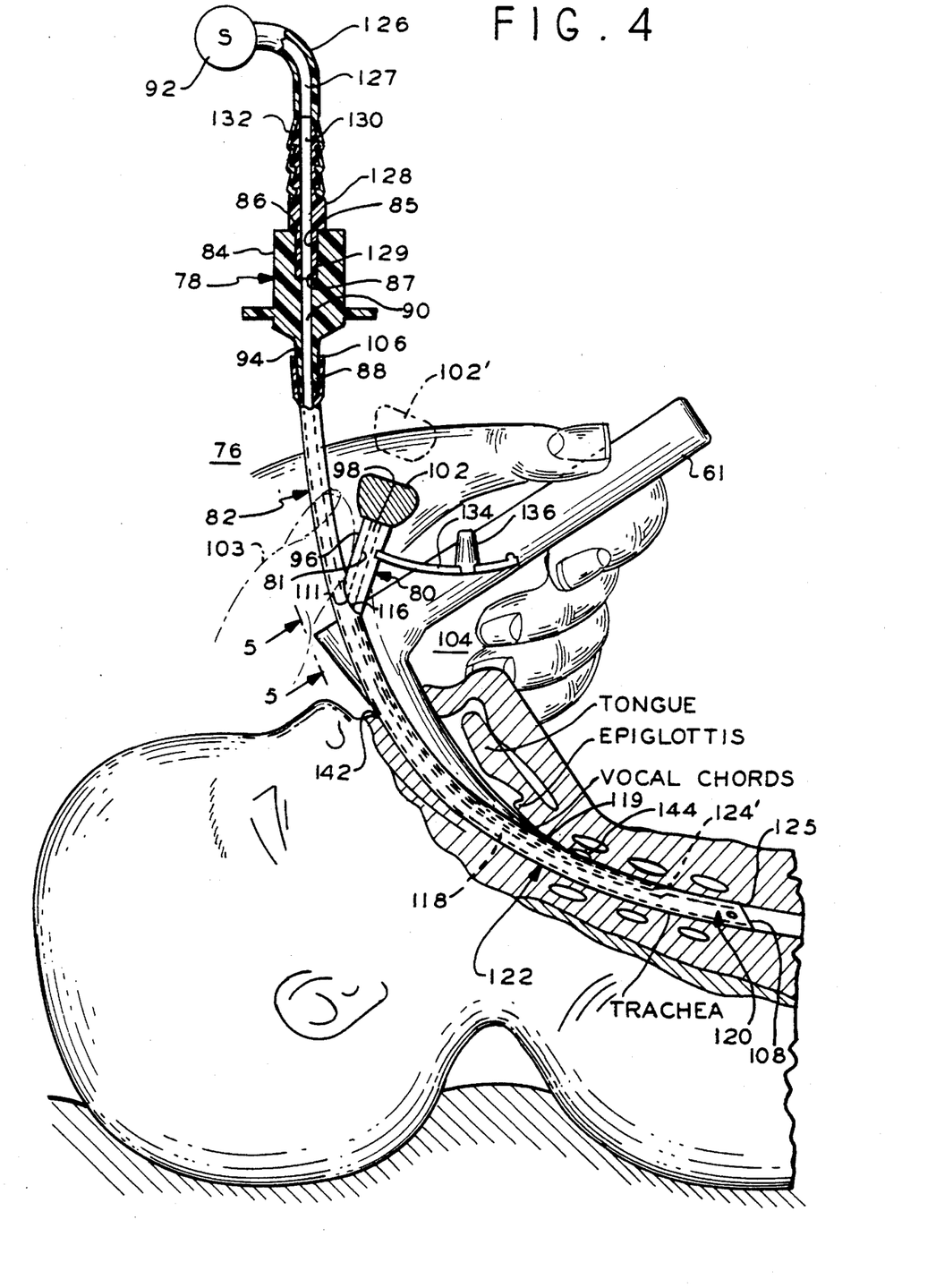
FIG. 4 is a side view of the resuscitation device while in use in the trachea of an infant shown partly in cross-section.

Rigid upper section 122 is curved to conform to the shape of the curvature between the entrance 142 to a newborn infant's mouth and the entrance 144 to the newborn's trachea (shown in FIG. 4). The curvature of the rigid upper section 122 is maintained by providing a shape support member 124, such as a cylindrical wire, in a secondary lumen 121 (shown in FIG. 3) in the outer wall 119 of the endotracheal tube 82. Although secondary lumen 121 extends the length of the endotracheal tube 82, the shape support member 124 only extends through secondary lumen 121 in the upper rigid section 122. The shape support member 124 may be mounted removably in the secondary lumen 121 to permit removal of the shape support member 124 so as to make the upper section 122 flexible; alternatively, the shape support member or wire 124 may be made a unitary or integral part of the upper section 122 by being suitably molded therein, or the shape support member may be inserted in the secondary lumen 121 into the position shown in FIG. 4 and the secondary lumen 121 suitably sealed to maintain the member 124 in the position shown in FIG. 4.

The flexible lower section 120 extends from the end of the rigid upper section 122 to the distal end of the endotracheal tube 82 at exit port 108.

The venting port 116 forms an opening in the inner curvature (top) of endotracheal tube 82 and communicates directly with main lumen 118. Venting port 116 is located at a point on endotracheal tube 82 which remains outside of the newborn infant's mouth when the resuscitation device is being used.

Referring to FIGS. 4, 5, 7, 8 and 9 the resuscitation device 76 is shown with attached connector 78 and lower adapter 80 to facilitate use in suctioning, providing oxygen, removing carbon dioxide, and providing medication to the neonatal patient.

The connector 78 includes a main cylinder 84, which has a main entrance opening 86 at the top, an intermediate opening 87 and a main exit opening 88 at the bottom. The main cylinder 84 is provided with a conduit 85 between the main entrance opening 86 and the intermediate opening 87 and with a conduit 90 between secondary opening 87 and main exit opening 88. The main cylinder 84 may be a standard 15 millimeter size or connector, i.e. a connector known to the art including an outer enlarged portion having a 15 mm outer diameter (OD), such that it may be easily connected to or detached from an outside suction source 92 or an oxygen source such as the standard ambu bag 93 shown in FIG. 6. The main cylinder 84 contains a tapered end 94 at the main exit opening 88.

The connector 78 is designed such that conduit 90 has a cross-sectional area substantially equal to that of the secondary opening 87 and the main exit opening 88; the main entrance opening 86 of the connector 78 has a cross-sectional area which is substantially equal to the cross-sectional area of the tapered end 129 of the adapter 128 to snugly receive the same.

The suction tubing adapter 128 is a "Christmas-tree" type adapter having a tapered end 129 designed to fit snugly within main entrance opening 86 of connector 78 so as to provide a conduit 130, between the conduit 90 of connector 78 and the lumen 127 of the suction tubing 126. Suction tubing 126 fits over the "Christmas-tree" end 132 of suction tubing adapter 128 and is provided with an internal passageway 127. The suction tubing passageway 127 and the suction tubing adapter conduit 130 have cross-sectional areas substantially equal to that of the connector conduit 90 and these features minimize or substantially eliminate any collection of secretions, and meconium, between the suction tubing 126, the suction tubing adapter 128 and the connector 78.

Figure 5:
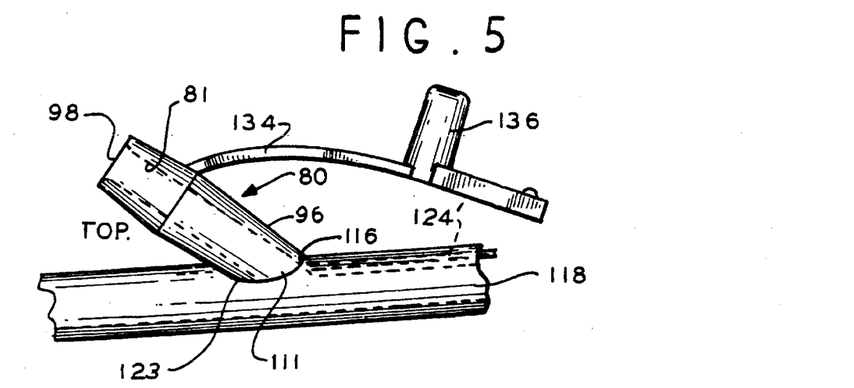
FIG. 5 is a side view of the endotracheal tube and lower adapter along the lines 5—5 in FIG. 4.

The lower adapter 80, FIGS. 4 and 5, includes a secondary cylinder 96, which has a passageway 81 extending therethrough which is opened between the top portion which forms a normally unoccluded secondary entrance opening 98 (the secondary entrance opening 98 is normally unoccluded in the sense that when the endotracheal tube 82 is inserted in an infant and a suction source 92 is connected to the endotracheal tube and when a syringe 100 is not inserted into the adapter 80) and the bottom portion which forms a secondary exit opening 111. Secondary exit opening 111 is connected with a venting port 116 on the inner curvature (top) of endotracheal tube 82. Venting port 116 extends through the outer wall 119 of endotracheal tube 82 and lower adapter 80 is bonded to the outer wall 119 of endotracheal tube 82 by a bonding or adhesive process so as to seal the edges 123 of lower adapter 80 to the outer wall 119 of endotracheal tube 82 and to allow a continuous flow of air or liquid to pass between secondary entrance opening 98 and lumen 118 of the endotracheal tube 82. To maximize the efficient use of lower adapter 80, it should extend upwardly with respect to the longitudinal axis of the endotracheal tube 82 and optimally be at an angle of about 45° with respect to the longitudinal axis of the endotracheal tube 82.

The secondary entrance opening 98, secondary exit opening 111, and venting port 116 on endotracheal tube 82 all have substantially the same cross-sectional area as lumen 118 of the endotracheal tube 82. These cross-sectional areas are the same to ensure that the negative suction pressure at the exit port 108 of endotracheal tube 82 is minimal when exit port 108 is occluded and when secondary opening 98 of lower adapter 80 is not occluded and suction is applied to main entrance opening 86. This will allow insertion of the endotracheal tube 82 into the trachea without suction being applied to the vocal cords or the tracheal wall during the intubation process if secondary entrance opening 98 is not occluded.

Figures 6, 7, 8, 9:
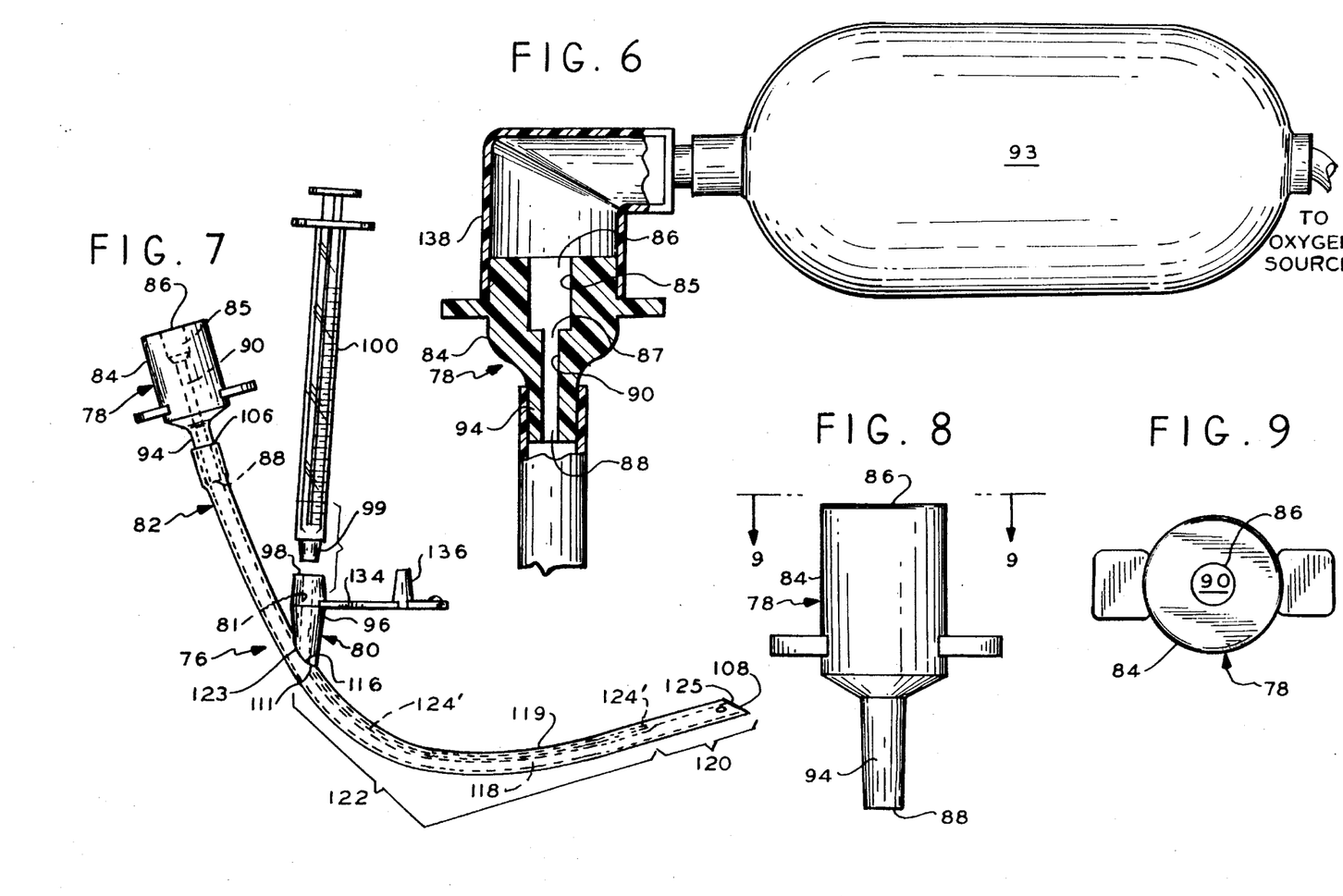
FIG. 6 is a side view, partly in cross-section, of an ambu bag attached to the connector and endotracheal tube.
FIG. 7 is a side view of a medication syringe as used with the adapter of the endotracheal tube.
FIG. 8 is a side view of the connector.
FIG. 9 is a top view of the connector along the lines 9—9 in FIG. 8.

In order to ensure that there is no suction or minimal suction at distal port 108, FIGS. 4 and 7, the cross-sectional area of the conduit 81, FIG. 4, through lower adapter 80 should be at least 80% of the cross-sectional area of lumen 118. It is preferred that these cross-sectional areas be substantially the same or that the cross-sectional area of the conduit 81 through lower adapter 80 be about 1.0 to 2.0 times the cross-sectional area of lumen 118. The cross-sectional area of the lumen 118 should be sufficient to easily allow the passage therethrough of the thick viscous meconium during suctioning. Typically, the cross-sectional area of lumen 118 is equivalent of a tube having an internal diameter of about 3.5 mm. However, lumen size may range from about 3.0 mm to about 4.0 mm. The outside diameter of endotracheal tube 82 is about 4.8 mm. but may range from about 4.0 to 5.5 mm.

The secondary entrance opening 98 is sized so as to snugly receive the end 99 of a standard medication syringe 100 or some other means of dispensing a medication to the patient through the endotracheal tube 82. For example, a standard Luer-type connector may be used for lower adapter 80 (see FIG. 7). The lower adapter 80 should be positioned in the endotracheal tube 82 so that the secondary entrance opening 98 remains outside of the patient's mouth when the endotracheal tube is being used to suction the patient.

Typically, the secondary entrance opening 98 should remain about 0 to 5 cm., preferably 1 to 3 cm., outside of the patient's mouth during suctioning.

The user will hold the endotracheal tube 82 at a point adjacent the lower adapter 80 so that he may, using a single hand, control the intubation and suctioning with the endotracheal tube 82, as well as control the degree of suction at exit port 108.

It should be recognized in embodiments in which there is no lower adapter 80, venting port 116 will serve the same function as secondary entrance opening 98. In these embodiments, venting port 116 should be maintained outside of the patient's mouth during suctioning. As with secondary entrance opening 98, venting port 116 should remain about 0 to 5 cm., preferably about 1 to 3 cm. outside of the patient's mouth.

The lower adapter 80 also has an attached flexible extension 134 attached near secondary entrance opening 98 with a plug 136 near the distal end of the extension. The plug 136 is sized so as to snugly fit into and occlude the secondary entrance opening 98 when desired. The plug will be inserted during ambu bag ventilation except when medications are being administered. The secondary entrance opening 98 can also be selectively occluded in whole or part with the finger tip of the resuscitating physician. The tip 102 of the right hand index finger of the user is shown in FIG. 4 occluding secondary entrance opening 98. In phantom, the tip 102' is positioned so that the secondary entrance opening 98 is open.

The endotracheal tube 82 is elongated and cylindrical in shape. The endotracheal tube contains first and second lumens 118 and 121 respectively. The main lumen 118 extends through the length of the endotracheal tube 82 between entry port 106 and distal exit port 108. The entry port 106 is sized to fit around tapered end 94 of connector 78 so that there is an open passageway from main entrance opening 86 and conduit 90, to main exit opening 88 through entry port 106, lumen 118 and out of exit port 108. The lumen 118 is elongated and substantially cylindrical in shape.

The endotracheal tube 82 has a flexible lower section 120 and a substantially rigid upper section 122 (see FIGS. 1 and 2). The rigid upper section 122 is shaped to conform to the curvature between a newborn infant's mouth and trachea. Typically this shape will have a radius of curvature of about 4 to 20 cm., preferably about 5 to 7 cm. and optimally about 5 cm.

A wire 124', substantially round in cross-section, may be used as the shape support member 124 to maintain the curvature of rigid upper section 122. The wire 124' is friction fit into secondary lumen 121 of endotracheal tube 82. Secondary lumen 121 extends through the length of endotracheal tube 82 but the wire 124' extends through secondary lumen 121 only in the upper rigid section 122. The secondary lumen 121 is within the outer wall 119 in the inside curvature (or top) of endotracheal tube 82. The upper rigid section 122 should be at least as long as the distance of the pathway between the mouth 142 and the trachea entrance 144 of the neonatal infant, as measured along the inner curvature (top) of the endotracheal tube 82. That distance is generally about 10 cm. but may range between about 8 and 12 cm. Therefore, the rigid upper section 122 should be at least 8 cm. long. The wire 124' may extend beyond venting port 116 toward the entry port 106 to a point near or at the proximate end of the endotracheal tube 82. In this case, the wire 124' will pass across venting port 116 as it extends in the outer wall 119 toward the proximate end of endotracheal tube 82. Since the wire 124' is small, it will not interfere with the function of venting port 116.

In the preferred embodiment the shape support member 124 is stainless steel 304 and has a tensile strength of about 105,000 to about 145,000 psi as determined by ASTM 313; the diameter of the wire is from about 0.002 to about 0.032 inch. It has been discovered that such tensile strength range provides the upper section 122 of the neonatal resuscitation device or apparatus of the present invention with a rigidity sufficient to maintain the upper section curved to conform to the shape of curvature of the pathway between the entrance 142 to a newborn infant's mouth and the entrance 144 to the newborn infant's trachea as shown in FIG. 4, but with a rigidity which does not pose a threat to injure or damage such pathway during insertion of the device. It will be further understood that the tensile strength range of the shape support member 124 is chosen such that the support member is sufficiently malleable or bendable that a physician or other user of the device can manually pre-shape the support member with the curvature desired to cause the endotracheal tube to conform to the curvature of the above-noted pathway of the newborn infant's trachea as the physician or other user views the infant. This permits the physician or other user to modify the shape of the endotracheal tube to more closely conform to the curvature of the pathway between the mouth and trachea of each specific newborn infant depending on the relative size of each specific newborn infant as viewed by the physician or other user. However, it will be understood that upon the shape support member being bent or shaped to conform to the curvature of a specific pathway, the shape support member is still sufficiently rigid to cause the tube to maintain the curvature provided by the physician on an infant-by-infant basis.

A round wire is not the only way to maintain the curvature of the rigid upper section 122. Other types of a shape supporting member 124 may be used such as an elongated member having a flat or oval shaped cross-section. Also, the shape supporting member 124 does not have to be friction fit into a secondary lumen 121. It may also be, for example, embedded in the wall of the endotracheal tube during the molding process. However, the shape support member 124 should not be within lumen 118 where it will interfere with the suctioning process.

The rigid upper section 122 can also be formed, for example, by coating the upper section of the endotracheal tube with substantially stiffer materials, such as epoxy resins, over the desired length to support the required curvature. Also, the endotracheal tube 82 can be formed from materials having differing flexibilities. A material having a rigidity which will maintain the desired curvature may be used to form the rigid upper section 122 and then that section may be bonded to the flexible lower section 120 which is soft and flexible.

Since the endotracheal tube 82 may be made from a flexible material such as PVC or polyurethane having a flexibility typically in the range of about 50 to 90 durometer, according to Shore A a hardness standard known to those skilled in the art, the flexible lower section 120 will not injure the tissues of the mouth, pharynx, larynx or trachea.

The distal edge 125 of the endotracheal tube 82 which forms exit port 108 is cut on an angled bias from top to bottom, the inside angle of which, with respect to the longitudinal axis of the endotracheal tube 82, is about 30° to 60°, preferably about 45°. The distal edge 125 is finished by a method such as RF heating to round the distal edge so as to minimize the risk of injury to the patient.

Generally, in embodiments containing a lower adapter 80 and in which the shape support member 124 extends above the venting port 116, the endotracheal tube 82 is about 12 to 19 cm. long, preferably about 14 to 17 cm.long and optimally about 16 cm.long. The distance from the main exit opening 108 to the distal end of the tube 82 to the venting port 116 is about 9 to 14 cm. preferably 10 to 12 cm. and optimally about 11 cm. The lower adapter 80 is about 1 to 3 cm. long, preferably about 2 cm. long. The distance from the main entrance opening 86 at the proximal end of the endotracheal tube 82 to the venting port 116 is about 3 to 5 cm., preferably 5 cm. The rigid upper section 122 extends from the proximate end of the endotracheal tube 82 toward the distal end for a distance of 8 to 18 cm., preferably about 15 cm. The flexible lower section 120 is about 0.5 to 5 cm., preferably about 1 to 2 cm. and optimally, about 1 cm. long.

In embodiments in which there is no lower adapter 80, the distance from the main exit port 108 in the distal end of the endotracheal tube 82 to the venting port 116 is about 11 to 15 cm., preferably about 13 cm.

In embodiments in which the shape support member 124 extends from the flexible lower section 120 to a point below venting opening 116, the rigid upper section will be about 8 to 12 cm., optimally about 10 cm., if the resuscitation device 76 includes a lower adapter 80, and about 10 to 14 cm., optimally 12 cm., if the resuscitation device does not include a lower adapter 80.

Unless otherwise stated, all lengths are measured along the internal curvature (top) of endotracheal tube 82.

As shown in FIG. 6, when the source of suction 92 is detached, an ambu bag 93 can be attached to connector 78 by fitting the ambu bag connector 138 over connector 78. The ambu bag 93 is then capable of supplying oxygen into the patient, and removing carbon dioxide from the patient, through endotracheal tube 82. An outside oxygen source such as an oxygen tank is contemplated.

The operation of the resuscitation device 76 is shown in FIG. 4. Suctioning with the resuscitation device 76 is carried out by attaching connector 78 to a source of suction 92 such as a mechanical device to provide suction. The source of suction 92 is connected through suction tubing 126 and suction tubing adapter 128 which fits into main cylinder 84 of connector 78, thereby creating an area of suction at exit port 108 when secondary entrance opening 98 is occluded.

In operation, the user holds a laryngoscope 61 in the left hand and deflects the tongue of the neonatal infant patient in order to visualize the hypopharynx of the patient. The resuscitation device 76 which is connected to a source of suction 92 through suction tubing 126 is held in the right hand at the section of the endotracheal tube 82 adjacent the lower adapter 80 (or venting port 116 if the device does not include lower adapter 80). Typically, the user will grasp the endotracheal tube 82 by putting the right hand thumb 103 on the outside curvature (bottom) of the endotracheal tube 82 and the right hand middle finger 104 (shown in phantom) at the base of lower adapter 80 (or directly below venting port 116 if the device does not include lower adapter 80). The secondary entrance opening 98 (or venting port 116) may then selectively be covered or uncovered by the tip 102 of the right hand index finger.

With the secondary entrance opening 98 occluded with the tip 102 of a finger of the right hand so as to create suction at exit port 108, the mouth and pharynx are then suctioned with the resuscitation device 76 which allows the user to visualize the vocal cords when the laryngoscope 61 is in position. When visualization of the vocal cords is achieved, the finger tip 102 is lifted (to the position shown as finger tip 102') from the secondary entrance opening 98 so as to minimize or eliminate the suction at the exit port 108. By allowing air to enter through secondary entrance opening 98 and minimizing the negative pressure at exit port 108, the endotracheal tube 82 can be inserted past the vocal cords into the trachea without exerting suction on the vocal cords and on the soft tissues of the trachea. This will minimize the chance of trauma to the vocal cords and the trachea during the intubation process and also allow for easier insertion of the endotracheal tube 82. The endotracheal tube 82 is commonly inserted 2 to 5 cm. past the vocal cords into the trachea. Since the flexible lower section 120 of the endotracheal tube 82 is not reinforced with a wire stylet, it is flexible and will not puncture or traumatize the infant's trachea. The rigid upper section 122 of the endotracheal tube 82 is reinforced with a wire 124' inserted into the secondary lumen 121 during the manufacturing process. Prior to insertion into the patient's mouth, the rigid upper section 122 of endotracheal tube 82 is curved to a shape which substantially conforms to the curvature of the pathway between the patient's mouth and trachea to facilitate intubation. The rigidity of the upper section 122 allows the lower flexible section 120 to be supported so that the user can easily direct the distal edge 125 of the endotracheal tube past the vocal cords and into the trachea.

Additionally, since the upper section 122 of the endotracheal tube is rigid and self-supporting, an intubation stylet that occludes the lumen of the endotracheal tube in the prior art devices is no longer needed. Because the intubation stylet of the prior art is no longer needed, the lumen remains open and the mouth and pharynx can be suctioned with the same endotracheal tube that will be used to intubate and suction meconium. In the prior art, an additional suction catheter was needed to clear the mouth and pharynx of secretions in order to be able to visualize the vocal cords before intubation.

Furthermore, since the upper section 122 of the endotracheal tube is rigid and self-supporting and does not require an intubation stylet, it is not necessary to remove the laryngoscope 61 after intubation in order to free the left hand to remove an intubation stylet used in the prior art.

Because the laryngoscope 61 can be left in place throughout the resuscitation process and an intubation stylet does not need to be inserted and removed and suction tubing does not need to be connected and disconnected, multiple passes of the endotracheal tube may be made into the trachea in a fraction of the time this operation took using the prior art devices. This allows a far more rapid, thorough, safer, and technically easier resuscitation.

The benefits of this new method are even more dramatic when one considers that each neonatal meconium resuscitation requires between two and four intubations before the infant is allowed to take its first breath. The longer the infant is prevented from taking its first breath, the greater the risk of damage to the infant from lack of oxygen.

After the distal edge 125 of the endotracheal tube 82 is inserted into the trachea, the index finger tip 102 covers the secondary entrance opening 98, thereby creating suction at exit port 108. The user then slowly withdraws the endotracheal tube 82 from the trachea with the secondary entrance opening 98 occluded throughout the withdrawal process. During the withdrawal process, meconium is cleared from the trachea.

After the endotracheal tube 82 is removed from the trachea, the user lifts his finger tip 102 (to the position shown as tip 102') from secondary entrance opening 98 so as to minimize the suction at exit port 108. The intubation procedure is again repeated as described. Typically, a complete resuscitation requires two to four intubations in order to completely clear the trachea of meconium.

Once the meconium is cleared from the infant's trachea, the patient requires ventilation to provide oxygen to and remove carbon dioxide from the lungs. While this can often be done with an ambu bag and mask held over the infant's face, it is far more effective to provide oxygen and remove carbon dioxide from the infant's lungs via an endotracheal tube. In the prior art, an additional endotracheal tube and intubation stylet was required. The entire intubation process would be repeated again, the stylet removed, and an ambu bag connected to the proximal end of the endotracheal tube.

Using the resuscitation device 76 of the present invention, after the meconium is cleared from the trachea, the distal edge 125 of endotracheal tube 82 can be reinserted into the trachea immediately since the vocal cords are continually visualized. At this point the laryngoscope 61 is removed, suction tubing adapter 128 is detached from connector 78 to discontinue suction in the endotracheal tube 82, and connector 78 is connected to a source of oxygen through an ambu bag 93 (see FIG. 6) to provide oxygen through the endotracheal tube 82 to the infant. While providing ambu bag ventilation, the secondary entrance opening 98 is occluded either with the finger tip 102 of the user's left hand or by inserting plug 136 connected by flexible extension 134 into the secondary entrance opening 98.

In some instances, a newborn infant patient's heart rate may remain dangerously slow even after the administration of oxygen. In such a circumstance, medication must be instilled directly into the patient's lungs via an endotracheal tube (see FIG. 7).

In the prior art, in order to introduce medication into the patient's lungs, the ambu bag must be disconnected from the endotracheal tube, thereby temporarily interrupting the supplying of oxygen to the infant. Using the resuscitation device 76, medications are administered through the endotracheal tube 82 by connecting a device, for example, a syringe 100, to secondary entrance opening 98 without an interruption of oxygenation.

While the device and the method have been described as being useful in assisting the treatment of infant patients who have aspirated meconium, it should be understood that the device and method may be used with any neonatal patient in need of having oxygen or medication administered to the air passageway or in need of having the air passageway suctioned.

Figures 10, 11:
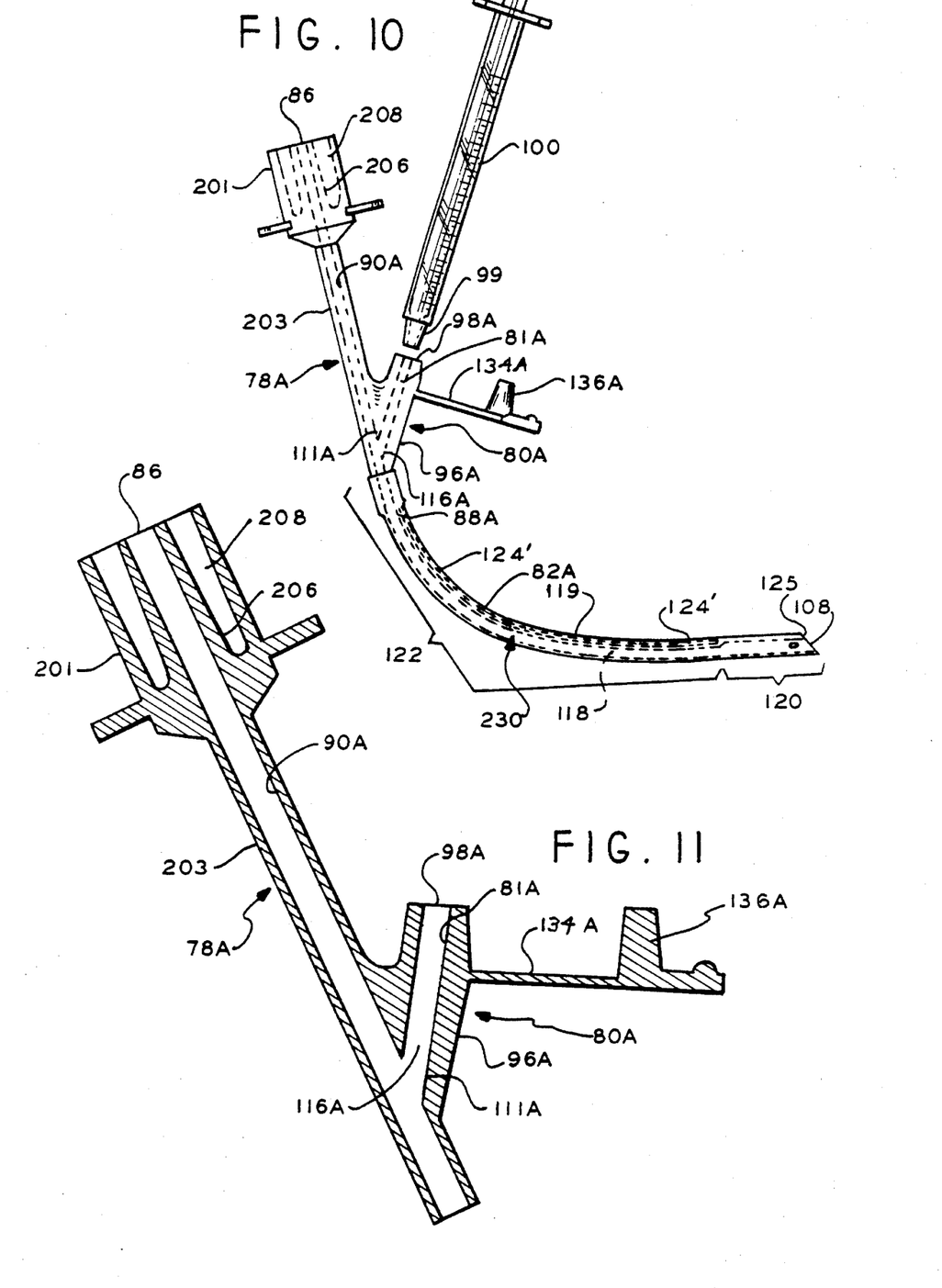
FIG. 10 is a side view of an alternate embodiment of the present invention for suctioning a neonatal infant and which embodiment is alternate to that shown in FIG. 7.
FIG. 11 is an enlarged cross-sectional view of the connector shown in the upper portion of FIG. 10.
Figure 12:
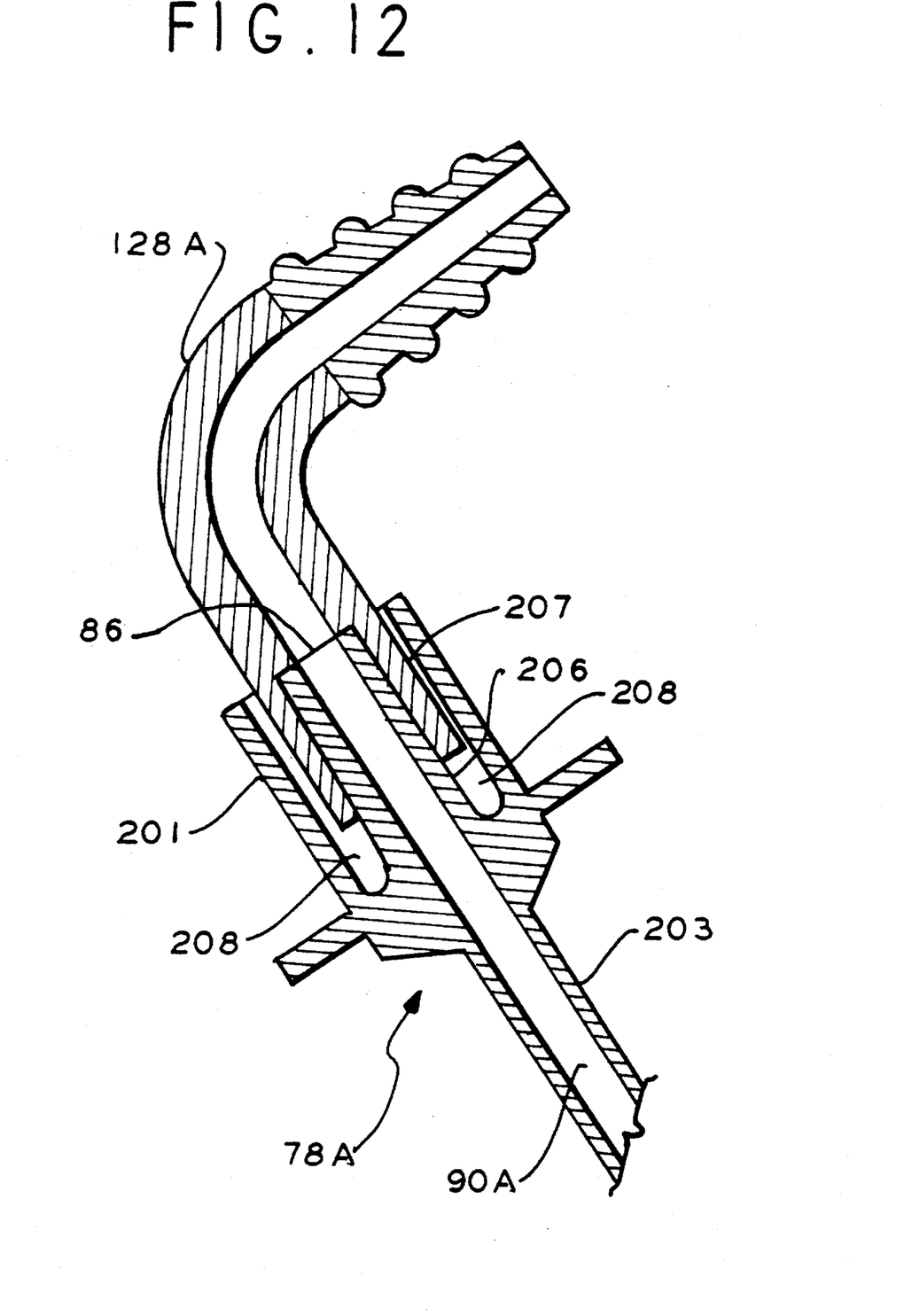
FIG. 12 is a partial cross-sectional view of the upper portion of the connector shown in FIG. 11 and shows such upper portion in interconnection with a suction tube adapter also shown in cross-section and which suction tube adapter is for being connected to a source of suction.

Referring to FIGS. 10–12, a further alternate embodiment of the neonatal resuscitation device of the present invention is shown. This embodiment is alternate to the embodiment of the present invention shown in FIGS. 4 and 7 and described above. Further, it will be generally understood that the alternate embodiment of FIGS. 10–12 functions in substantially the same manner as the embodiment shown in FIGS. 4 and 7, and for convenience of reference structural elements shown in FIGS. 10–12 which are the same as the elements shown in FIGS. 4 and 7 are given the same numerical designations and structural elements shown in FIGS. 10–12 which correspond to or function substantially the same as elements shown in FIGS. 4 and 7 are given the same numerical designations as in FIGS. 4 and 7 with the addition of the letter A. Like the embodiment shown in FIGS. 4 and 7, the neonatal resuscitation device embodiment shown in FIGS. 10–12 is for being connected to a source of suction such as the source of suction 92 shown in FIG. 4, for suctioning meconium from the pharynx and trachea of a neonatal infant and for alternately being connected to a source of oxygen, such as for example the ambu bag 93 shown in FIG. 6, to supply oxygen to, and remove carbon dioxide from, the infant.

It will be generally understood that the primary difference between the alternate embodiment shown in FIGS. 10–12 and the embodiment shown in FIGS. 4 and 7 is that the lower adapter 80A and the venting port 116A which remain outside the mouth of the neonatal infant during suctioning are located on the lower cylindrical portion 203 of the connector 78A instead of being located on the endotracheal tube 82 as shown in FIGS. 4 and 7.

Referring now particularly to the alternate embodiment shown in FIGS. 10–12, the neonatal resuscitation device includes an endotracheal tube 82A including an upper section 122 and a lower section 120. As with regard to the early embodiment shown in FIGS. 4 and 7, the lower section 120 is flexible and shorter in length than the upper section 122 and the upper section 122 includes at least a portion as shown in FIG. 10 which is rigid, or at least substantially rigid, for a length of at least the length of and a curvature substantially conforming to the curvature of the pathway from the mouth to the trachea of the neonatal infant and which curved pathway is illustrated in FIG. 4. The upper section 122 of the endotracheal tube 82A may be provided with such rigidity and curvature by a shape support member or wire 124' as shown in FIGS. 4 and 7 and described above.

The connector indicated by numerical designation 78A is alternate to the connector 78 shown in FIGS. 4 and 7 and connector 78A includes an upper portion 201 for being connected to a source of suctioning as will be described with regard to FIG. 12 or to a source of oxygen such as the ambu bag 93 shown in FIG. 6; thus it will be understood that the connector upper portion is generally in the shape of a standard 15 mm connector having a 15 mm OD. The upper connector portion 201 is provided with an annular post 206 and an annular slot 208 to facilitate connection to a suction tube adapter such as the L-shaped suction tube adapter 128A shown in FIG. 12; the L-shaped suction tube adapter 128A shown in FIG. 12 is also a "Christmas-tree" adapter of the type described above for connection to suction tubing such as suction tubing 126 shown in FIG. 4. The connector 78A includes a cylindrical lower portion 203 whose lower extremity is for being connected to the upper or proximal portion of the endotracheal tube 82A as shown in FIG. 10. Connector 78A is provided with a centrally formed internal conduit 90A and it will be understood that conduit 90A and the main lumen 118 formed internally of the endotracheal tube 82A combine to form a combined passageway indicated by general numerical designation 230 in FIG. 10 for suctioning a neonatal infant and for supplying oxygen to, or removing carbon dioxide from, the neonatal infant. The combined passageway 230 may be, and preferably is, uniform in cross-section along its length to minimize, or substantially eliminate, the collection of meconium therein.

It will be further understood that in the alternate embodiment of FIGS. 10–12 the relative sizes of the cross-sectional areas of the conduit 90A, main lumen 118, venting port 116A, secondary entrance opening 98A and secondary exit opening 111A of the lower adapter 80A are the same as for the corresponding structure shown in FIGS. 4 and 7 and described above. The passageway 81A extending through the lower adapter 80A, FIG. 10, is in fluid communication with the combined passageway 230 and the entrance opening 98A of the passageway 81A may be used to vent the combined passageway 230 in the same manner as described above with regard to the venting of the main lumen 118 shown in FIGS. 4 and 7. The endotracheal tube 82A may be manufactured as described above with regard to endotracheal tube 82 and the connector 78A may be molded from a suitable plastic in the manner known to the art and is therefore rigid, or at least substantially rigid, and is provided with the shape shown in FIGS. 10–12.

The radius of curvature provided by the shape support member or wire 124' to the upper section 122 of the endotracheal tube 82A, FIG. 10, is about 5 to about 7 cm. preferably about 5 cm. The length of the upper section 122 of the endotracheal tube 82A is about 8 to about 12 cm. preferably 10 cm. The length of the lower section 120 of the endotracheal tube 82A is about 0.5 to about 2 cm. preferably 1 cm. The length of the connector 78A is about 5 to about 7 cm. preferably about 6 cm.

As taught above with regard to lower adapter 80 of FIGS. 4 and 7, the secondary entrance opening 98A, FIG. 10, conduit or passageway 81A, secondary exit opening 111A of the lower adapter 80A and the venting port 116A should be at least 80% of the cross-sectional area of the main lumen 118 of the endotracheal tube 82A and, as taught above, it is preferred in the embodiment of FIGS. 10–12 that such cross-sectional area of the passageway 81A through the lower adapter 80A be about 1.0 to 2.0 times the cross-sectional area of the main lumen 118 of the endotracheal tube 82A. The cross-sectional areas are measured perpendicular to the longitudinal axis of each conduit, passageway or lumen and the cross-sectional area of the main lumen 118 of the endotracheal tube 82A should be sufficient to easily allow the passage of the thick viscous meconium during suctioning. The entrance 98A to the adapter passageway 81A may be sized to be larger than the end 99 of the standard medication syringe 100 to permit easy entry of the syringe end 99 at least partially into the passageway 81A to facilitate dispensing of medication through the passageway 81A and through the combined passageway 230 to the infant. The adapter passageway 81A may be round or oval in cross-section. Further the adapter passageway 81A and the combined passageway 230 may be sized, in cross-section to permit the introduction of a standard suction catheter into the passageway 81A, through the combined passageway 230 and out the opening 108 to the infant's lungs.

The cross-sectional areas referred to herein are transverse cross-sectional areas taken or measured perpendicular to the longitudinal axis of each part, lumen, conduit or passageway.

The terms and expressions employed are terms of description and not of limitation and there is no intention in using such terms and expressions of excluding any equivalents of the features shown and described. It is recognized that various modifications are possible within the scope of the invention claimed.

What is claimed is:

1. Apparatus for resuscitating a neonatal infant having a mouth, a trachea and a pathway extending from the mouth into the trachea, and the pathway having a length and a curvature, comprising:

a generally elongated endotracheal tube including a wall and having a proximate end and a distal end and including an upper section and a lower section shorter in length than said upper section, said lower section being flexible and said upper section including a portion which is substantially equal in length to the length of the pathway;

a curved, rigid shape support member mounted in said wall of said endotracheal tube, said support member substantially conforming to the curvature of the pathway and said support member making said upper section of said endotracheal tube substantially rigid and providing said upper section with a curvature substantially conforming to the curvature of the pathway;

a rigid connector including a rigid cylindrical upper portion for being connected to a mechanical source of suctioning or a source of controlled mechanical ventilation connected to a source of oxygen the source of mechanical ventilation for controlling the provision of oxygen to and removal of carbon dioxide from the infant, and a rigid cylindrical lower portion connected to said proximate end of said endotracheal tube, said upper and lower portions being integral, said rigid cylindrical upper portion having a first outer diameter and said rigid cylindrical lower portion having a second outer diameter smaller than said first outer diameter;

said endotracheal tube having at least a first lumen extending therethrough and said connector having a conduit extending therethrough, said first lumen and said conduit connected and combining to form a combined passageway having a substantially uniform cross-section, throughout its length, for suctioning or ventilating and supplying oxygen to or removing carbon dioxide from the infant; and an adapter provided on said rigid cylindrical lower portion of said connector and said adapter provided with an adapter passageway in fluid communication with said combined passageway, said adapter provided at a location which remains outside of the mouth of the infant while the infant is being resuscitated and said adapter passageway provided with an entrance opening for venting said combined passageway to substantially eliminate suction at said distal end of said endotracheal tube during insertion of said endotracheal tube into the pathway and while said endotracheal tube is connected to the source of suctioning, said adapter passageway permitting the dispensing of liquid medicine therethrough into said combined passageway and into the infant while said endotracheal tube is connected to the source of controlled mechanical ventilation, and said combined passageway and said adapter passageway having cross-sections sufficiently large to permit the insertion therethrough of a suctioning catheter while said endotracheal tube is connected to the source of controlled mechanical ventilation.

2. The apparatus according to claim 1 wherein said adapter extends outwardly and upwardly with respect to said lower portion of said connector.

3. The apparatus according to claim 2 wherein said adapter forms an acute angle with respect to said lower portion of said connector.

4. The apparatus according to claim 3 wherein said acute angle is about 45°.

5. The apparatus according to claim 3 or 4 wherein said acute angle is about 45°.

6. The apparatus according to claim 1 wherein said shape support member has a radius of curvature which said shape support member imparts to said upper section of said endotracheal tube and wherein said radius of curvature is about 4 cm. to about 20 cm.

7. The apparatus according to claim 6 wherein said radius of curvature is about 5 cm. to about 7 cm.

8. The apparatus according to claim 7 wherein said radius of curvature is about 5 cm.

9. The apparatus according to claim 1 wherein said upper section of said endotracheal tube has a length of about 8 cm. to about 12 cm.

10. The apparatus according to claim 9 wherein said length is about 10 cm.

11. The apparatus according to claim 1 wherein the length of said lower section of said endotracheal tube is about 0.5 cm. to about 2 cm.

12. The apparatus according to claim 11 wherein said length is about 1 cm.

13. The apparatus according to claim 1 wherein said connector has a length of about 5 cm. to about 7 cm.

14. The apparatus according to claim 13 wherein said length is about 6 cm.

15. The apparatus according to claim 1 wherein said adapter passageway has a cross-sectional area, wherein said combined passageway has a cross-sectional area and wherein the cross-sectional area of said adapter passageway is at least 80% of the cross-sectional area of said combined passageway.

16. The apparatus according to claim 15 wherein said cross-sectional area of said adapter passageway is about 1.0 to about 2.0 times the cross-sectional area of said combined passageway.

17. The apparatus according to claim 1 wherein said adapter passageway is oval in cross-section.

18. The apparatus according to claim 1 wherein said adapter passageway is round in transverse cross-section.

19. The apparatus according to claim 1 wherein said entrance opening of said adapter passageway has a size which permits the insertion of the end of a standard medication syringe at least partially into said adapter passageway to facilitate the dispensing of medication to the infant through said adapter passageway and through said combined passageway to the infant while said endotracheal tube is connected to said source of controlled mechanical ventilation.

20. The apparatus according to claim 1 wherein said entrance opening of said adapter passageway is sufficiently large to receive an end of a standard medication syringe to permit the insertion of said end of said standard medication syringe at least partially into said adapter passageway to facilitate the dispensing of medication to the infant through said adapter passageway and through said combined passageway to the infant while said endotracheal tube is connected to the source of controlled mechanical ventilation.

21. The apparatus according to claim 1 wherein the infant has lungs and wherein said adapter passageway and said combined passageway are sized in cross-section to be sufficiently large to permit the introduction of a standard suction catheter into said adapter passageway and through said combined passageway and into the lungs of the infant.

22. The apparatus according to claim 1 wherein said combined passageway is uniform in cross-section to substantially eliminate the collection of meconium therein.

23. The apparatus according to claim 1 wherein said upper portion of said connector is in the shape of a standard 15 mm connector and wherein said first outer diameter is 15 mm.

24. The apparatus according to claim 1 wherein said shape support member has a tensile strength of about 105,000 psi to about 145,000 psi.

25. The apparatus according to claim 1 wherein said endotracheal tube has a second lumen extending therethrough at least along the length of said upper section and extending substantially parallel to said first lumen, wherein said shape support member is a wire having a length substantially equal to the length of said upper section and wherein said wire is mounted in said second lumen.

26. The apparatus according to claim 25 wherein said wire has a tensile strength of about 105,000 psi to about 145,000 psi.

27. The apparatus according to claim 26 wherein said wire has a diameter of about 0.002 to about 0.032 inch.

28. The apparatus according to claim 27 wherein said endotracheal tube has a radius of curvature and wherein said radius of curvature is about 4 to about 20 cm.

29. The apparatus according to claim 24 wherein said adapter passageway has a cross-sectional area, wherein said combined passageway has a cross-sectional area and wherein the cross-sectional area of said adapter passageway is at least 80% of the cross-sectional area of said combined passageway.

30. The apparatus according to claim 29 wherein said cross-sectional area of said adapter passageway is about 1.0 to about 2.0 times the cross-sectional area of said combined passageway.

31. The apparatus according to claim 24 wherein said adapter passageway is round in cross-section.

32. The apparatus according to claim 24 wherein said adapter passageway is oval in cross-section.

33. The apparatus according to claim 24 wherein said adapter passageway has an entrance opening sized to snugly fit the end of a standard medication syringe to permit the insertion of the end of the standard medication syringe into said adapter passageway to facilitate the dispensing of medication to the infant through said adapter passageway and through said combined passageway to the infant.

34. The apparatus according to claim 24 wherein said adapter passageway has an entrance opening larger than the size of the end of a standard medication syringe to permit the insertion of the end of the standard medication syringe into said adapter passageway to facilitate the dispensing of medication to the infant through said adapter passageway and through said combined passageway to the infant.

35. The apparatus according to claim 24 wherein the infant has lungs and wherein said adapter passageway and said combined passageway are sized in cross-section to be sufficiently large to permit the introduction of a standard suction catheter into said adapter passageway and through said combined passageway and into the lungs of the infant.

36. The apparatus according to claim 24 wherein said combined passageway is uniform in cross-section to substantially eliminate the collection of meconium therein.

37. The apparatus according to claim 24 wherein said upper portion of said connector has the shape of a standard 15 mm connector and wherein said first outer diameter is 15 mm.

38. Apparatus for resuscitating a neonatal infant having a mouth, a trachea and a pathway extending from the mouth into the trachea, and the pathway having a length and a curvature, comprising:

a generally elongated endotracheal tube including a wall and having a proximate end and a distal end and including an upper section and a lower section shorter in length than said upper section, said lower section being flexible and said upper section including a portion which is substantially equal in length to the length of the pathway;

a curved substantially rigid shape support member mounted in said wall of said endotracheal tube, said shape support member being sufficiently bendable to permit said endotracheal tube to be pre-shaped to a desired curvature prior to intubation of the infant with said endotracheal tube so as to provide said upper section with a curvature substantially conforming to the curvature of the pathway, said shape support member making said upper section of said endotracheal tube sufficiently rigid so as to maintain the desired curvature while said endotracheal tube is in use during the resuscitation;

a rigid connector including integrally formed rigid cylindrical upper and lower portions, said upper portion having a first outer diameter, and said lower portion having a second outer diameter smaller than said first outer diameter, said outer diameter of said upper portion of a size to facilitate connection to a mechanical source of suctioning or a source of controlled mechanical ventilation connected to a source of oxygen, the source of mechanical ventilation for controlling the provision of oxygen to, and removal of carbon dioxide from the infant, said rigid connector having a conduit extending therethrough;

said endotracheal tube having at least a first lumen extending therethrough, said first lumen and said conduit extending through said connector connected and combining to form a combined passageway having a substantially uniform cross-section, throughout its length, for suctioning or ventilating and supplying oxygen to, or the removal of carbon dioxide from the infant; and an adapter provided on said rigid cylindrical lower portion of said connector and said adapter provided with an adapter passageway in fluid communication with said combined passageway, said adapter provided at a location which remains outside of the mouth of the infant while the infant is being resuscitated and said adapter passageway provided with an entrance opening for venting said combined passageway to substantially eliminate suction at said distal end of said endotracheal tube during insertion of said endotracheal tube into the pathway and while said endotracheal tube is connected to the source of suctioning, said adapter passageway permitting the dispensing of liquid medicine therethrough into said combined passageway and into the infant while said endotracheal tube is connected to the source of controlled mechanical ventilation, and said combined passageway and said adapter passageway having cross-sections sufficiently large to permit the insertion therethrough of a suctioning catheter while said endotracheal tube is connected to the source of controlled mechanical ventilation.

39. The apparatus according to claim 38 wherein said upper portion of said rigid connector is provided with an inwardly extending annular slot facilitating connection to a source of suction.

* * * * *

UNITED STATES PATENT AND TRADEMARK OFFICE
CERTIFICATE OF CORRECTION

PATENT NO. : 5,509,408
DATED : April 23, 1996
INVENTOR(S) : Peter S. Kurtis

It is certified that error appears in the above-indentified patent and that said Letters Patent is hereby corrected as shown below:

ABSTRACT, line 6, after "length" insert --than--.

Column 1, line 29, "breath" should be --breathe--.

Signed and Sealed this

Third Day of September, 1996

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,509,408
DATED : April 23, 1996
INVENTOR(S) : Peter S. Kurtis

It is certified that error appears in the above-indentified patent and that said Letters Patent is hereby corrected as shown below:

On the title page: Item [73]Assignee should read -- Vital Signs, Inc., Totowa, N. J. --.

ABSTRACT, line 6, after "length" insert --than--.

Column 1, line 29, "breath" should be --breathe--.

Signed and Sealed this

Fifteenth Day of October, 1996

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,509,408
DATED : April 23, 1996
INVENTOR(S) : Peter S. Kurtis

It is certified that error appears in the above-indentified patent and that said Letters Patent is hereby corrected as shown below:

Title page, item [73], Assignee: Delete "Vital Signs, Inc., Totowa, N.J.--.

Signed and Sealed this

Twenty-sixth Day of November 1996

Attest:

BRUCE LEHMAN

Attesting Officer     Commissioner of Patents and Trademarks